United States Patent
Han et al.

(10) Patent No.: US 6,984,521 B2
(45) Date of Patent: Jan. 10, 2006

(54) HEK293 CELL LINE FOR ACTIVITY STUDIES AND HTS SYSTEM OF $\alpha_{1G}$ T-TYPE $CA^{2+}$ CHANNEL

(75) Inventors: Ye Sun Han, Seoul (KR); Hyewhon Rhim, Seoul (KR); Taehyun Kim, Seoul (KR); Sunoh Kim, Seoul (KR); Dae-sik Lim, Daejeon (KR); Juhyun Choi, Bucheon-si (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 10/857,291

(22) Filed: May 28, 2004

(65) Prior Publication Data

US 2005/0130298 A1    Jun. 16, 2005

(30) Foreign Application Priority Data

Dec. 12, 2003    (KR) .................... 10-2003-0090518

(51) Int. Cl.
  C12N 5/08    (2006.01)
  C12N 5/00    (2006.01)
  C12P 21/06   (2006.01)
  C12P 1/06    (2006.01)

(52) U.S. Cl. ..................... 435/366; 435/325; 435/69.1; 435/6

(58) Field of Classification Search .................... 436/6; 435/41, 366, 325, 69.1, 6
See application file for complete search history.

(56) References Cited

OTHER PUBLICATIONS

Lee et.al., J. of Neurosci. 19: 1912-1921, 1992.*
Bernheim et.al., News Physiol. Sci. 17: 22-26,2002.*
Picones et.al., Biophysical journal 81:2035-2049, 2001.*
Cheng et.al., Blood, 92:83-82, 1998.*
Clontechniques, Jan. 1999.*

* cited by examiner

Primary Examiner—Janet Andres
Assistant Examiner—Gyan Chandra
(74) Attorney, Agent, or Firm—Jones Day

(57) ABSTRACT

There is provided a cell line that is prepared by transforming HEK293 cell with a human Kir2.1 gene using a retrovirus expression system, wherein the HEK293 expresses a stable $\alpha_{1G}$ T-type calcium channel. The cell line responds sensitively to KCl and forms an appropriate level of the membrane voltage so that the cell signaling pathway may be investigated by the molecular biological and biochemical studies.

1 Claim, 12 Drawing Sheets

```
1    ATGGGCAGTGTGCGAACCAACCGCTACAGCATCGTCTCTTCAGAAGAAGACGGTATGAAG  60
     M  G  S  V  R  T  N  R  Y  S  I  V  S  S  E  E  D  G  M  K
61   TTGGCCACCATGGCAGTTGCAAATGGCTTTGGGAACGGGAAGAGTAAAGTCCACACCCGA  120
     L  A  T  M  A  V  A  N  G  F  G  N  G  K  S  K  V  H  T  R
121  CAACAGTGCAGGAGCCGCTTTGTGAAGAAAGATGGCCACTGTAATGTTCAGTTCATCAAT  180
     Q  Q  C  R  S  R  F  V  K  K  D  G  H  C  N  V  Q  F  I  N
181  GTGGGTGAGAAGGGGCAACGGTACCTCGCAGACATCTTCACCACGTGTGTGGACATTCGC  240
     V  G  E  K  G  Q  R  Y  L  A  D  I  F  T  T  C  V  D  I  R
241  TGGCGGTGGATGCTGGTTATCTTCTGCCTGGCTTTCGTCCTGTCATGGCTGTTTTTTGGC  300
     W  R  W  M  L  V  I  F  C  L  A  F  V  L  S  W  L  F  F  G
301  TGTGTGTTTTGGTTGATAGCTCTGCTCCATGGGGACCTGGATGCATCCAAAGAGGGCAAA  360
     C  V  F  W  L  I  A  L  L  H  G  D  L  D  A  S  K  E  G  K
361  GCTTGTGTGTCCGAGGTCAACAGCTTCACGGCTGCCTTCCTCTTCTCCATTGAGACCCAG  420
     A  C  V  S  E  V  N  S  F  T  A  A  F  L  F  S  I  E  T  Q
421  ACAACCATAGGCTATGGTTTCAGATGTGTCACGGATGAATGCCCAATTGCTGTTTTCATG  480
     T  T  I  G  Y  G  F  R  C  V  T  D  E  C  P  I  A  V  F  M
481  GTGGTGTTCCAGTCAATCGTGGGCTGCATCATCGATGCTTTCATCATTGGCGCAGTCATG  540
     V  V  F  Q  S  I  V  G  C  I  I  D  A  F  I  I  G  A  V  M
541  GCCAAGATGGCAAAGCCAAAGAAGAGAAACGAGACTCTTGTCTTCAGTCACAATGCCGTG  600
     A  K  M  A  K  P  K  K  R  N  E  T  L  V  F  S  H  N  A  V
601  ATTGCCATGAGAGACGGCAAGCTGTGTTTGATGTGGCGAGTGGGCAATCTTCGGAAAAGC  660
     I  A  M  R  D  G  K  L  C  L  M  W  R  V  G  N  L  R  K  S
661  CACTTGGTGGAAGCTCATGTTCGAGCACAGCTCCTCAAATCCAGAATTACTTCTGAAGGG  720
     H  L  V  E  A  H  V  R  A  Q  L  L  K  S  R  I  T  S  E  G
721  GAGTATATCCCTCTGGATCAAATAGACATCAATGTTGGGTTTGACAGTGGAATCGATCGT  780
     E  Y  I  P  L  D  Q  I  D  I  N  V  G  F  D  S  G  I  D  R
781  ATATTTCTGGTGTCCCCAATCACTATAGTCCATGAAATAGATGAAGACAGTCCTTTATAT  840
     I  F  L  V  S  P  I  T  I  V  H  E  I  D  E  D  S  P  L  Y
841  GATTTGAGTAAACAGGACATTGACAACGCAGACTTTGAAATCGTGGTCATACTGGAAGGC  900
     D  L  S  K  Q  D  I  D  N  A  D  F  E  I  V  V  I  L  E  G
901  ATGGTGGAAGCCACTGCCATGACGACACAGTGCCGTAGCTCTTATCTAGCAAATGAAATC  960
     M  V  E  A  T  A  M  T  T  Q  C  R  S  S  Y  L  A  N  E  I
961  CTGTGGGGCCACCGCTATGAGCCTGTGCTCTTTGAAGAGAAGCACTACTACAAAGTGGAC  1020
     L  W  G  H  R  Y  E  P  V  L  F  E  E  K  H  Y  Y  K  V  D
```

FIG.1a

1021 TATTCCAGGTTCCACAAAACTTACGAAGTCCCCAACACTCCCCTTTGTAGTGCCAGAGAC 1080
     Y  S  R  F  H  K  T  Y  E  V  P  N  T  P  L  C  S  A  R  D
1081 TTAGCAGAAAAGAAATATATCCTCTCAAATGCAAATTCATTTTGCTATGAAAATGAAGTT 1140
     L  A  E  K  K  Y  I  L  S  N  A  N  S  F  C  Y  E  N  E  V
1141 GCCCTCACAAGCAAAGAGGAAGACGACAGTGAAAATGGAGTTCCAGAAAGCACTAGTACG 1200
     A  L  T  S  K  E  E  D  D  S  E  N  G  V  P  E  S  T  S  T
1201 GACACGCCCCCTGACATAGACCTTCACAACCAGGCAAGTGTACCTCTAGAGCCCAGGCCC 1260
     D  T  P  P  D  I  D  L  H  N  Q  A  S  V  P  L  E  P  R  P
1261 TTACGGCGAGAGTCGGAGATA 1281
     L  R  R  E  S  E  I

FIG.1b

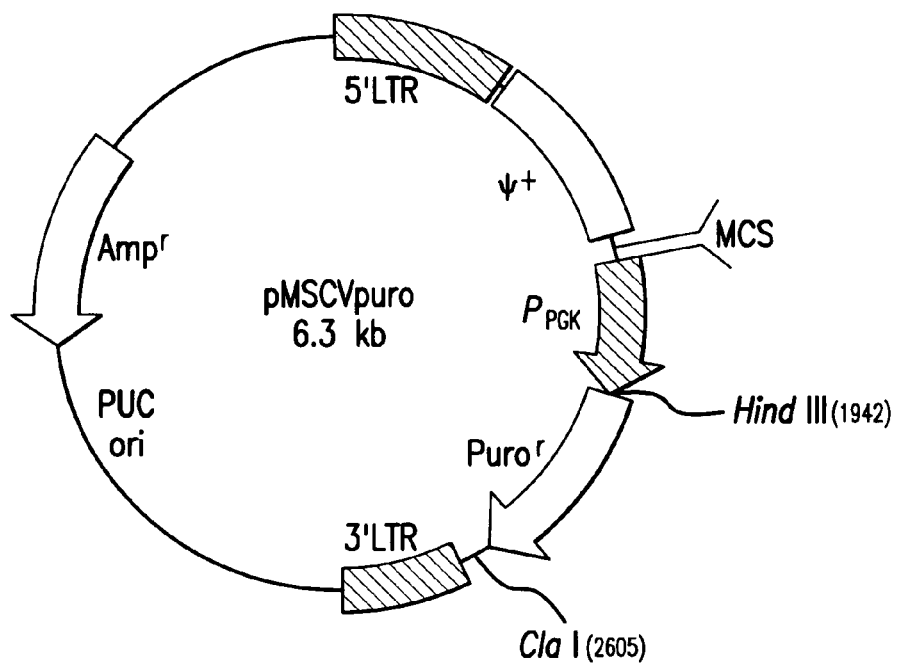
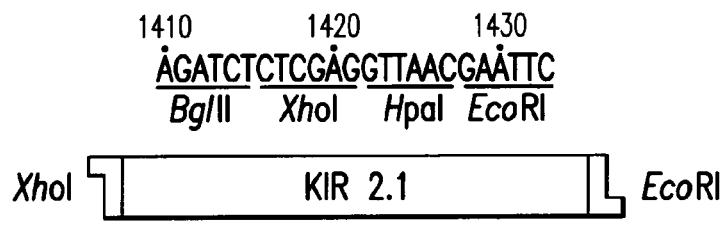
FIG.2
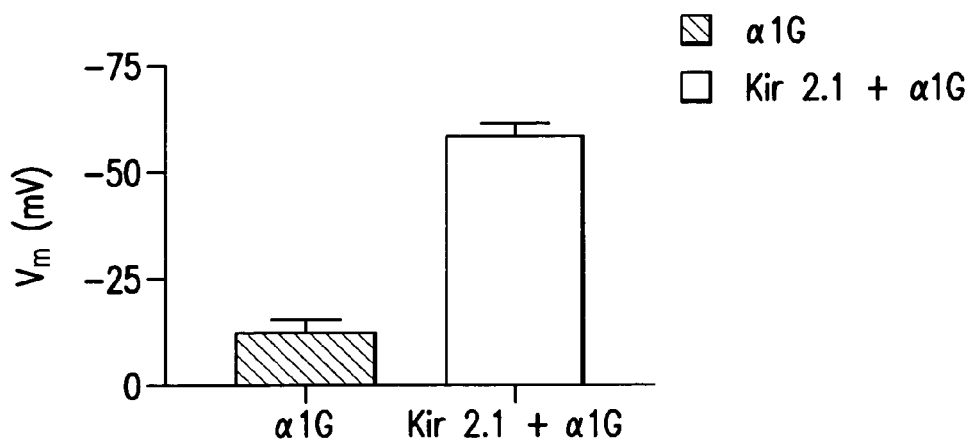
FIG.3

Kir 2.1 + α1G

α1G

Kir 2.1 + α1G

US 6,984,521 B2

SEQUENCE LISTING

```
<160> NUMBER OF SEQ ID NOS: 4

<210> SEQ ID NO 1
<211> LENGTH: 1284
<212> TYPE: DNA
<213> ORGANISM: human being
<220> FEATURE:
<221> NAME/KEY: CDS
<222> LOCATION: (1)..(1281)

<400> SEQUENCE: 1 atg ggc agt gtg cga acc aac cgc tac agc atc gtc tct tca gaa gaa      48
Met Gly Ser Val Arg Thr Asn Arg Tyr Ser Ile Val Ser Ser Glu Glu
 1               5                  10                  15 gac ggt atg aag ttg gcc acc atg gca gtt gca aat ggc ttt ggg aac      96
Asp Gly Met Lys Leu Ala Thr Met Ala Val Ala Asn Gly Phe Gly Asn
                20                  25                  30 ggg aag agt aaa gtc cac acc cga caa cag tgc agg agc cgc ttt gtg     144
Gly Lys Ser Lys Val His Thr Arg Gln Gln Cys Arg Ser Arg Phe Val
            35                  40                  45 aag aaa gat ggc cac tgt aat gtt cag ttc atc aat gtg ggt gag aag     192
Lys Lys Asp Gly His Cys Asn Val Gln Phe Ile Asn Val Gly Glu Lys
        50                  55                  60
```

-continued

| | |
|---|---|
| ggg caa cgg tac ctc gca gac atc ttc acc acg tgt gtg gac att cgc<br>Gly Gln Arg Tyr Leu Ala Asp Ile Phe Thr Thr Cys Val Asp Ile Arg<br>65                       70                    75                    80 | 240 |
| tgg cgg tgg atg ctg gtt atc ttc tgc ctg gct ttc gtc ctg tca tgg<br>Trp Arg Trp Met Leu Val Ile Phe Cys Leu Ala Phe Val Leu Ser Trp<br>                    85                    90                    95 | 288 |
| ctg ttt ttt ggc tgt gtg ttt tgg ttg ata gct ctg ctc cat ggg gac<br>Leu Phe Phe Gly Cys Val Phe Trp Leu Ile Ala Leu Leu His Gly Asp<br>                 100                  105                110 | 336 |
| ctg gat gca tcc aaa gag ggc aaa gct tgt gtg tcc gag gtc aac agc<br>Leu Asp Ala Ser Lys Glu Gly Lys Ala Cys Val Ser Glu Val Asn Ser<br>          115                120                125 | 384 |
| ttc acg gct gcc ttc ctc ttc tcc att gag acc cag aca acc ata ggc<br>Phe Thr Ala Ala Phe Leu Phe Ser Ile Glu Thr Gln Thr Thr Ile Gly<br>130                      135                  140 | 432 |
| tat ggt ttc aga tgt gtc acg gat gaa tgc cca att gct gtt ttc atg<br>Tyr Gly Phe Arg Cys Val Thr Asp Glu Cys Pro Ile Ala Val Phe Met<br>145                      150                  155                160 | 480 |
| gtg gtg ttc cag tca atc gtg ggc tgc atc atc gat gct ttc atc att<br>Val Val Phe Gln Ser Ile Val Gly Cys Ile Ile Asp Ala Phe Ile Ile<br>                 165                  170                175 | 528 |
| ggc gca gtc atg gcc aag atg gca aag cca aag aag aga aac gag act<br>Gly Ala Val Met Ala Lys Met Ala Lys Pro Lys Lys Arg Asn Glu Thr<br>              180                  185                190 | 576 |
| ctt gtc ttc agt cac aat gcc gtg att gcc atg aga gac ggc aag ctg<br>Leu Val Phe Ser His Asn Ala Val Ile Ala Met Arg Asp Gly Lys Leu<br>          195                200                205 | 624 |
| tgt ttg atg tgg cga gtg ggc aat ctt cgg aaa agc cac ttg gtg gaa<br>Cys Leu Met Trp Arg Val Gly Asn Leu Arg Lys Ser His Leu Val Glu<br>210                      215                  220 | 672 |
| gct cat gtt cga gca cag ctc ctc aaa tcc aga att act tct gaa ggg<br>Ala His Val Arg Ala Gln Leu Leu Lys Ser Arg Ile Thr Ser Glu Gly<br>225                      230                  235                240 | 720 |
| gag tat atc cct ctg gat caa ata gac atc aat gtt ggg ttt gac agt<br>Glu Tyr Ile Pro Leu Asp Gln Ile Asp Ile Asn Val Gly Phe Asp Ser<br>                 245                  250                255 | 768 |
| gga atc gat cgt ata ttt ctg gtg tcc cca atc act ata gtc cat gaa<br>Gly Ile Asp Arg Ile Phe Leu Val Ser Pro Ile Thr Ile Val His Glu<br>              260                  265                270 | 816 |
| ata gat gaa gac agt cct tta tat gat ttg agt aaa cag gac att gac<br>Ile Asp Glu Asp Ser Pro Leu Tyr Asp Leu Ser Lys Gln Asp Ile Asp<br>          275                280                285 | 864 |
| aac gca gac ttt gaa atc gtg gtc ata ctg gaa ggc atg gtg gaa gcc<br>Asn Ala Asp Phe Glu Ile Val Val Ile Leu Glu Gly Met Val Glu Ala<br>290                      295                  300 | 912 |
| act gcc atg acg aca cag tgc cgt agc tct tat cta gca aat gaa atc<br>Thr Ala Met Thr Thr Gln Cys Arg Ser Ser Tyr Leu Ala Asn Glu Ile<br>305                      310                  315                320 | 960 |
| ctg tgg ggc cac cgc tat gag cct gtg ctc ttt gaa gag aag cac tac<br>Leu Trp Gly His Arg Tyr Glu Pro Val Leu Phe Glu Glu Lys His Tyr<br>                 325                  330                335 | 1008 |
| tac aaa gtg gac tat tcc agg ttc cac aaa act tac gaa gtc ccc aac<br>Tyr Lys Val Asp Tyr Ser Arg Phe His Lys Thr Tyr Glu Val Pro Asn<br>              340                345                350 | 1056 |
| act ccc ctt tgt agt gcc aga gac tta gca gaa aag aaa tat atc ctc<br>Thr Pro Leu Cys Ser Ala Arg Asp Leu Ala Glu Lys Lys Tyr Ile Leu<br>          355                360                365 | 1104 |
| tca aat gca aat tca ttt tgc tat gaa aat gaa gtt gcc ctc aca agc<br>Ser Asn Ala Asn Ser Phe Cys Tyr Glu Asn Glu Val Ala Leu Thr Ser<br>370                      375                  380 | 1152 |

-continued

```
aaa gag gaa gac gac agt gaa aat gga gtt cca gaa agc act agt acg      1200
Lys Glu Glu Asp Asp Ser Glu Asn Gly Val Pro Glu Ser Thr Ser Thr
385                 390                 395                 400 gac acg ccc cct gac ata gac ctt cac aac cag gca agt gta cct cta      1248
Asp Thr Pro Pro Asp Ile Asp Leu His Asn Gln Ala Ser Val Pro Leu
                405                 410                 415 gag ccc agg ccc tta cgg cga gag tcg gag ata tga                      1284
Glu Pro Arg Pro Leu Arg Arg Glu Ser Glu Ile
                420                 425

<210> SEQ ID NO 2
<211> LENGTH: 427
<212> TYPE: PRT
<213> ORGANISM: human being

<400> SEQUENCE: 2

Met Gly Ser Val Arg Thr Asn Arg Tyr Ser Ile Val Ser Ser Glu Glu
 1               5                  10                  15

Asp Gly Met Lys Leu Ala Thr Met Ala Val Ala Asn Gly Phe Gly Asn
                20                  25                  30

Gly Lys Ser Lys Val His Thr Arg Gln Gln Cys Arg Ser Arg Phe Val
            35                  40                  45

Lys Lys Asp Gly His Cys Asn Val Gln Phe Ile Asn Val Gly Glu Lys
        50                  55                  60

Gly Gln Arg Tyr Leu Ala Asp Ile Phe Thr Thr Cys Val Asp Ile Arg
 65                 70                  75                  80

Trp Arg Trp Met Leu Val Ile Phe Cys Leu Ala Phe Val Leu Ser Trp
                85                  90                  95

Leu Phe Phe Gly Cys Val Phe Trp Leu Ile Ala Leu Leu His Gly Asp
                100                 105                 110

Leu Asp Ala Ser Lys Glu Gly Lys Ala Cys Val Ser Glu Val Asn Ser
            115                 120                 125

Phe Thr Ala Ala Phe Leu Phe Ser Ile Glu Thr Gln Thr Thr Ile Gly
        130                 135                 140

Tyr Gly Phe Arg Cys Val Thr Asp Glu Cys Pro Ile Ala Val Phe Met
145                 150                 155                 160

Val Val Phe Gln Ser Ile Val Gly Cys Ile Ile Asp Ala Phe Ile Ile
                165                 170                 175

Gly Ala Val Met Ala Lys Met Ala Lys Pro Lys Lys Arg Asn Glu Thr
                180                 185                 190

Leu Val Phe Ser His Asn Ala Val Ile Ala Met Arg Asp Gly Lys Leu
            195                 200                 205

Cys Leu Met Trp Arg Val Gly Asn Leu Arg Lys Ser His Leu Val Glu
        210                 215                 220

Ala His Val Arg Ala Gln Leu Leu Lys Ser Arg Ile Thr Ser Glu Gly
225                 230                 235                 240

Glu Tyr Ile Pro Leu Asp Gln Ile Asp Ile Asn Val Gly Phe Asp Ser
                245                 250                 255

Gly Ile Asp Arg Ile Phe Leu Val Ser Pro Ile Thr Ile Val His Glu
                260                 265                 270

Ile Asp Glu Asp Ser Pro Leu Tyr Asp Leu Ser Lys Gln Asp Ile Asp
            275                 280                 285

Asn Ala Asp Phe Glu Ile Val Val Ile Leu Glu Gly Met Val Glu Ala
        290                 295                 300

Thr Ala Met Thr Thr Gln Cys Arg Ser Ser Tyr Leu Ala Asn Glu Ile
```

-continued

```
            305                 310                 315                 320
    Leu Trp Gly His Arg Tyr Glu Pro Val Leu Phe Glu Glu Lys His Tyr
                    325                 330                 335

Tyr Lys Val Asp Tyr Ser Arg Phe His Lys Thr Tyr Glu Val Pro Asn
                    340                 345                 350

Thr Pro Leu Cys Ser Ala Arg Asp Leu Ala Glu Lys Lys Tyr Ile Leu
                    355                 360                 365

Ser Asn Ala Asn Ser Phe Cys Tyr Glu Asn Glu Val Ala Leu Thr Ser
                370                 375                 380

Lys Glu Glu Asp Asp Ser Glu Asn Gly Val Pro Glu Ser Thr Ser Thr
    385                 390                 395                 400

Asp Thr Pro Pro Asp Ile Asp Leu His Asn Gln Ala Ser Val Pro Leu
                    405                 410                 415

Glu Pro Arg Pro Leu Arg Arg Glu Ser Glu Ile
                    420                 425

<210> SEQ ID NO 3
<211> LENGTH: 29
<212> TYPE: DNA
<213> ORGANISM: Artificial Sequence
<220> FEATURE:
<223> OTHER INFORMATION: Description of Artificial Sequence: primer

<400> SEQUENCE: 3
ccgctcgagg ccgccatggg cagtgtgag                                      29

<210> SEQ ID NO 4
<211> LENGTH: 29
<212> TYPE: DNA
<213> ORGANISM: Artificial Sequence
<220> FEATURE:
<223> OTHER INFORMATION: Description of Artificial Sequence: primer

<400> SEQUENCE: 4
ccggaattct catatctccg attctcgcc                                      29
```

HEK293 CELL LINE FOR ACTIVITY STUDIES AND HTS SYSTEM OF $\alpha_{1G}$ T-TYPE $CA^{2+}$ CHANNEL This application claims benefit of Foreign Application REPUBLIC OF KOREA 10-2003-90518 filed on Dec. 12, 2003, which is hereby incorporated herein in its entirety.

FIELD OF THE INVENTION

The present invention relates generally to cell lines, and more particularly to a cell line that is prepared by transforming certain HEK293 cell with a human Kir2.1 gene using a retrovirus expression system.

BACKGROUND OF THE INVENTION

A membrane protein, voltage-dependent $Ca^{2+}$ channel controls various intracellular actions such as muscular contraction, nerve cell generation and synaptic plasticity, secretion of neutrotransmitter and hormone, and gene expression by regulating calcium ion influx from outside of a cell. As is well known in the art, such voltage-dependent calcium channel is divided into the two main groups based on the requirement voltage for opening channels: high-voltage-activated (HVA) and low-voltage-activated (LVA) $Ca^{2+}$ channels. Currently, HVA $Ca^{2+}$ channels are further divided into L-, N-, P/Q-, and R-types and these functional diversities are related to the existence of several $\alpha_1$ subunits ($\alpha_{1A-F}$ and $\alpha_{1s}$). LVA $Ca^{2+}$ channels are readily distinguished from HVA $Ca^{2+}$ channels because they activate at potential near the resting membrane potential and referred to as "transient (T)-type $Ca^{2+}$ channels" due to their fast inactivation and small conductance. Until recently, three genes encoding T-type $Ca^{2+}$ channel pore-forming subunits were identified and designated $Ca_v3.1$ ($\alpha_{1G}$), $Ca_v3.2$ ($a_{1H}$), and $Ca_v3.3$ ($a_{1I}$).

Among the above-noted calcium channels, the T-type calcium channel is known to have many functional aspects which are well defined in various printed publications. The functions of T-type calcium channel include and extend to, for instance, controlling the firing bursts of a nerve cell (See, Huguenard, J. R. et al., Annu. Rev. Physiol. 58, 329–348, 1996), pace maker activity of the heart (See, Zhou, Z & Lipsius, S. L. J. Mol. Cell. Cardiol. 26, 1211–1219, 1994), a hormone aldosterone secretion (See, Rossier, M. F. et al., Endocrinology 137, 4817–4826, 1996) and fertilization (See, Arnoult, C. et al., Proc. Natl. Acad. Sci. 93, 13004–13009, 1996).

T-type calcium channel that is quickly activated and inactivated due to a unique low conductivity typically becomes activated between the range of –40 to –30 mV. However, it is very crucial to maintain the cell membrane voltage prior to activation as it may lead to an undesired effect of rapid inactivation. Because the membrane voltage of most cells expressing the T-type calcium channel is not hyperpolarized sufficiently for activating the same, no methods for studying the membrane voltage currently exist with the exception of an electrophysiological method.

Therefore, studies on signaling pathway mechanism of T-type calcium channel in the nerve cell and scientific researches for developing T-type calcium channel inhibitors are severely undermined. In this respect, it is technically unfeasible, if not impossible, to study and research the T-type calcium channels without resorting to the traditional electrophysiological method. As such, new and innovative methods are needed to improve and enhance the study of the T-type calcium channels.

SUMMARY OF THE INVENTION

The object of the present invention is to create a certain cell line that can be utilized in scientific studies and/or researches on developing T-type calcium channel inhibitors, and further in screening such inhibitors with a high level of efficiency by activating the T-type calcium channel through changing the extracellular KCl concentration.

In the cell line of the present invention, $\alpha_{1G}$ T-type calcium channel becomes activated by a high concentration of KCl through expressing the potassium channel. This greatly functions to form a membrane voltage in the human embryonic kidney (HEK293) cell line that expresses the $\alpha_{1G}$ T-type calcium channel stably and consistently so as to lower the membrane voltage toward hyperpolarization and to further stabilize the membrane voltage.

Thus, the cell line of the present invention is prepared by transforming the HEK293 cell with the human potassium inwardly-rectifying channel (Kir2.1 gene (SEQ ID NO: 1) using a retrovirus expression system. However, it is imperative and thus should be noted herein that the HEK293 cell expresses $\alpha_{1G}$ T-type calcium channel prior to its transformation with the human Kir2.1 gene.

More specifically, the present invention is directed to a cell line that is prepared by transforming HEK293 cell, stably expressing $\alpha_{1G}$ T-type calcium channel, with a plasmid containing the human Kir2.1 gene. Preferably, the HEK293 cell is transformed with a plamid shown and represented in FIG. 2 using a retrovirus expression system

BRIEF DESCRIPTION OF THE DRAWINGS

FIG. 1 shows a base sequence of the human Kir2.1 gene and an amino acid sequence corresponding thereto.

FIG. 2 shows a plasmid pMSCVpuro containing the whole human Kir2.1 gene.

FIG. 3 is a graph showing the membrane voltage of HEK293 cell selectively expressing only $\alpha_{1G}$ T-type calcium channel ($\alpha_{1G}$ HEK293 cell, control group) and HEK293 cell co-expressing $\alpha_{1G}$ T-type calcium channel and Kir 2.1 (Kir2.1+$\alpha_{1G}$ HEK293 cell);

FIG. 4a and FIG. 4b are graphs illustrating the current-voltage correlation between $\alpha_{1G}$ HEK293 cell and Kir2.1+$\alpha_{1G}$ HEK293 cell. FIG. 4c and FIG. 4d show practical current curves of $\alpha_{1G}$ HEK293 cell and Kir2.1+$\alpha_{1G}$ HEK293 cell at each voltage. FIG. 4e and FIG. 4f are graphs showing expression of Kir2.1 in Kir2.1+$\alpha_{1G}$ HEK293 cell by an inhibitive level on $Ba^{2+}$ and $Cs^+$ known as Kir2.1 inhibitor.

FIG. 5a and FIG. 5b are graphs illustrating the current-voltage correlation between $\alpha_{1G}$ HEK293 cell and Kir2.1+$\alpha_{1G}$ HEK293 cell for $\alpha_{1G}$ T-type calcium channel activity. FIG. 5c and FIG. 5d show practical current curves of $\alpha_{1G}$ HEK293 cell and Kir2.1+$\alpha_{1G}$ HEK293 cell at each voltage. FIG. 5e and FIG. 5f are graphs illustrating the current versus concentration of $Ni^{2+}$ known as $\alpha_{1G}$ T-type calcium channel inhibitor of $\alpha_{1G}$ HEK293 cell and Kir2.1+$\alpha_{1G}$ HEK293 cell. FIG. 5g and FIG. 5h are graphs showing the current versus mibefradil concentration of $\alpha_{1G}$ HEK293 cell and Kir2.1+$\alpha_{1G}$ HEK293 cell.

FIG. 6a and FIG. 6b are graphs showing the activation/inactivation of T-type calcium channel gate of $\alpha_{1G}$ HEK293 cell and Kir2.1+$\alpha_{1G}$ HEK293 cell.

DETAILED DESCRIPTION OF THE PRESENT INVENTION

Figure 4A:
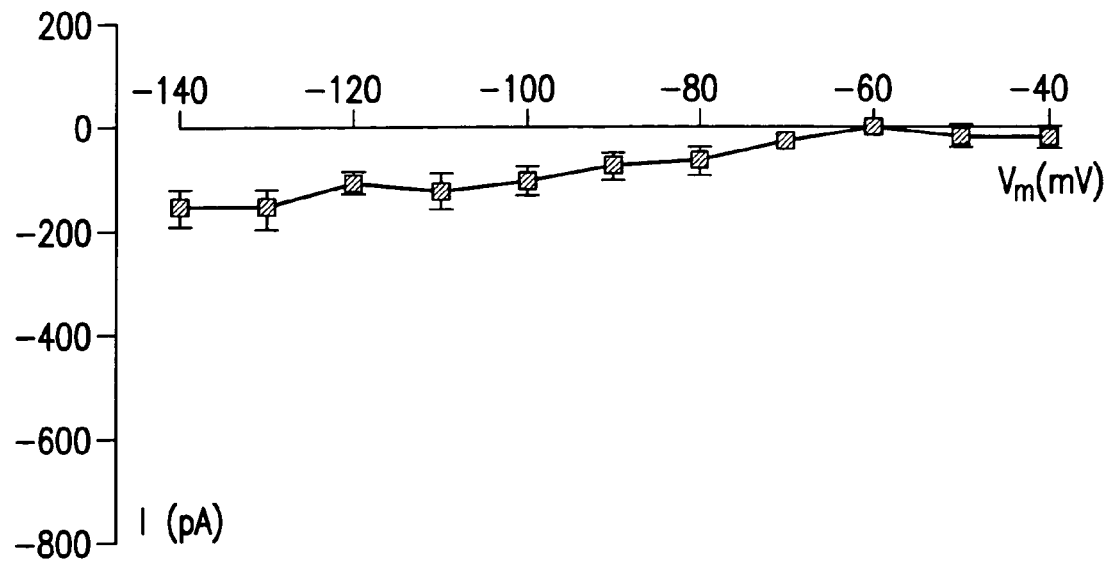
FIGS. 4a–4f show the results confirming Kir2.1 expression in Kir2.1+$\alpha_{1G}$ HEK293 cell by using an electrophysiological whole-cell patch-clamp method.
Figure 4B:
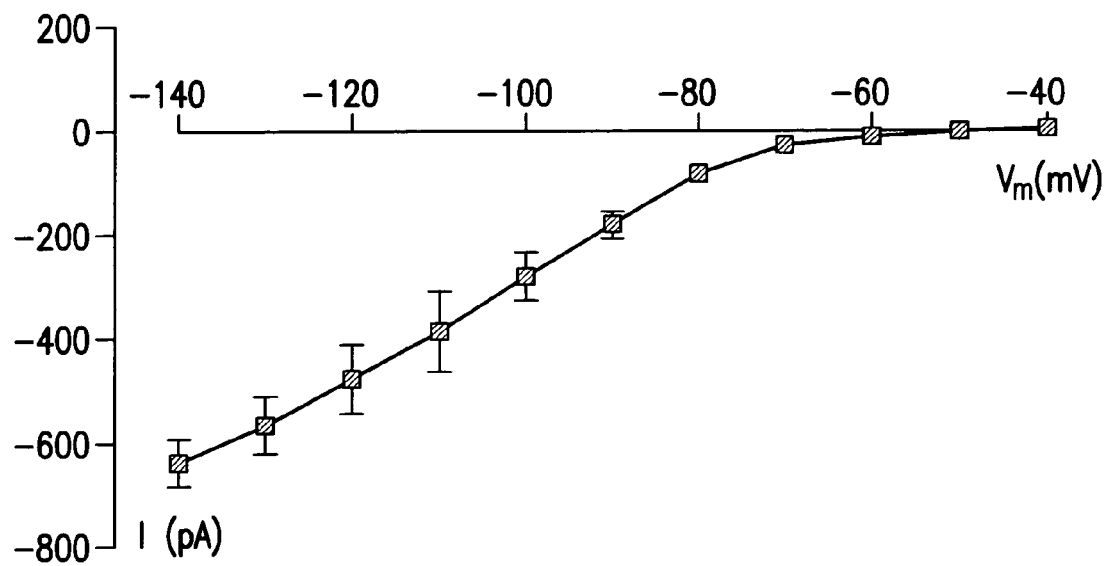
Figure 4C:
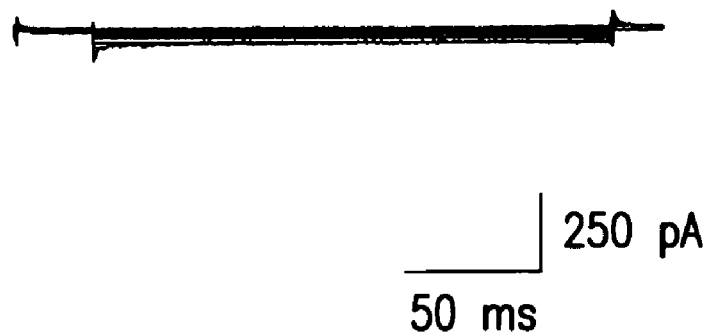
Figure 4D:
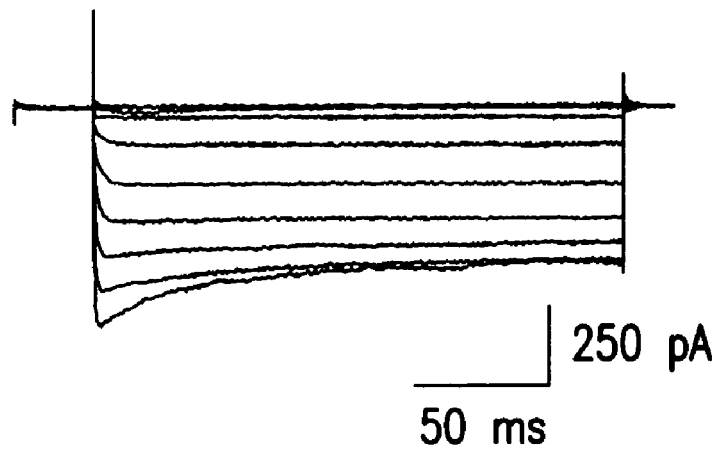

The present invention is directed to a cell line that is prepared by transforming HEK293 cell with a human Kir2.1 gene using a retrovirus expression system. It should be specifically noted herein that HEK293 cell expresses $\alpha_{1G}$ T-type calcium channel stably and consistently prior to its transformation with the human Kir2.1 gene.

The cell line of the present invention has a T-type calcium channel which becomes activated by treatment with a high concentration of KCl. The present cell line was deposited as a human embryonal kidney cell line (293 cell) in the Korean Collection for Type Cultures, No. 52, Oun-dong, Yusong-ku, Taejon 305–333, Republic of Korea, on Sep. 29, 2003 and was assigned accession No. KCTC 10519BP.

The cell line of the present invention was first established by using HEK293 cell line which expresses $\alpha_{1G}$ T-type calcium channel stably and steadily. It is recognized that HEK293 cell line having such stable $\alpha_{1G}$ T-type calcium channel was originated from Edward Perez-Reyes of University of Virginia (Lee, J. H. et al., J. Neurosci. 19, 1912–1921, 1999).

In the preferred embodiment of the present invention, the human Kir2.1 gene (SEQ. ID. NO. 1) was treated with the restriction enzymes XhoI and EcoRI. The human Kir2.1 gene was then introduced into pMSCVpuro which was treated with the same enzymes to prepare plasmid Kir2.1-pMSCVpuro. The obtained plasmid was used to transfect a wild type of HEK293 cell and the transfected cells were cultured. The culture was mixed with a culture supernatant of the HEK293 cell line which expressed $\alpha_{1G}$ T-type calcium channel stably and incubated to obtain the cell line of the present invention expressing stable Kir2.1.

To determine whether the cell line of the present invention forms a stable membrane voltage by Kir2.1 expression, an electrophysiological perforated patch-clamp method was used to determine the cell membrane voltage and the biophysical and pharmacological properties of the expressed Kir2.1. The previously expressed $\alpha_{1G}$ T-type calcium channel were confirmed by whole cell patch-clamp method. Finally, to identify that T-type calcium channel can become activated merely by treatment with a high concentration KCl, change of intracellular calcium ion concentration was determined by using fura-2 AM dye.

The cell line of the present invention generates an appropriate level of membrane voltage capable of responding to KCl sensitively due to Kir2.1 expression and thus only T-type calcium channel is activated. Therefore, the present cell line can provide the basis for investigating T-type calcium channel in a different way from the traditional electrophysiological method.

The present invention is further described with the following examples which should not be construed as limiting the present invention. It should be recognized herein that additional modifications and improvements within the spirit and scope of the present invention may be apparent and contemplated.

EXAMPLE 1

Cell Line and Culture Method

The cell line of the present invention was first created by using HEK293 cell line which already expresses $\alpha_{1G}$ T-type calcium channel stably and consistently. As briefly mentioned above, such cell line had been established by and originated from Edward Perez-Reyes of University of Virginia. The experiments were carried out by using the cell line ($\alpha_{1G}$ HEK293) expressing stable $\alpha_{1G}$ T-type calcium channel as a control and the HEK293 cell line of the present invention (Kir2.1+$\alpha_{1G}$ HEK293) expressing stable Kir2.1 with $\alpha_{1G}$ T-type calcium channel.

The culture medium of the control was prepared by adding 10% fetal bovine serum and 1% penicillin/streptomycin (v/v) to Dulbecco's modified Eagle's medium (DMEM), and the cell was incubated in a vessel under a humidified condition of 95% air/5% $CO_2$ at or about 37° C. The culture medium was exchanged with a fresh medium once in 3–4 days and the cell was sub-cultured each week. A solution of geneticin selective antibiotic, G-418 (0.5 mg/ml), was used to grow only the cell which expressed $\alpha_{1G}$ T-type calcium channel.

The culture medium of Kir2.1+$\alpha_{1G}$ HEK293 cell line was prepard by further adding puromycin (1 µg/ml) to the medium of the control and the culture condition was the same as the control. The cells used in determining T-type calcium channel activity were recorded 2–7 days after culturing the cells on a cover slip coated with poly-L-lysine (0.5 mg/ml) in each sub-culturing.

EXAMPLE 2

Retrovirus Expression System

The whole base sequence of human Kir2.1 gene shown in FIG. 1 (SEQ. ID. NO. 1) was cloned into pMSCVpuro (Clontech, FIG. 2).

To obtain a base sequence of Kir2.1, the plasmid cDNA library (Takara) was subjected to PCR with the cycle profiles: 1 cycle of about 5 min at approximately 95° C.; 30 cycles of about 30 sec at approximately 95° C., about 30 sec at approximately 55° C. and about 2 min at approximately 72° C.; and 1 cycle of about 7 min at approximately 72° C. by using Kir2.1 XhoI Forward primer (SEQ. ID. NO. 3) and Kir2.1 RI Reverse primer (SEQ. ID. NO. 4).

Kir2.1 XhoI Forward primer (SEQ. ID. NO. 3);
5'-ccgctcgaggccgccatgggcagtgtgag-3'
Kir2.1 RI Reverse primer (SEQ. ID. NO. 4);
5'-ccggaattctcatatctccgattctcgcc-3'

The obtained Kir2.1 gene was treated with XhoI and EcoRI restriction enzymes. The Kir2.1 gene was then introduced into pMSCVpuro which was treated with the same enzymes to prepare plasmid Kir2.1-pMSCVpuro.

The obtained plasmid was used to prepare the HEK293 cell line in which Kir2.1 was expressed stably as described below.

The wild type HEK293 cells of about 2.6×10⁶ were plated on 6 cm culture dish and grown in a chamber in which DMEM (supplemented with 0.1 mM non-essential amino acids and 10% FBS, culture condition; 37° C., a humidified mixture of 95%:5% (v/v) air and $CO_2$) was filled. After about 18 hours, the cell line was transfected with a solution that was obtained by precipitating Kir2.1-pMSCVpuro (FIG. 2) 6 µg, pEQPAM3 (Clontech) 3 µg and pVSV-G (Clontech) 3 µg in 0.5 M of aqueous calcium solution, and the medium was exchanged with a fresh medium after about 6 hours. After about 20 hours incubation, the medium was exchanged with 3 ml of the medium. After about 20 hours, the culture of the wild type HEK293 cell transfected with such Kir2.1-pMSCVpuro was centrifuged at about 2,000 rpm for approximately 10 minutes. The supernatant of 2.5 ml was mixed with polybrene (Sigma) in a final concentration of 6 mg/ml.

Separately, the HEK293 cell line of about $2 \times 10^5$ and expressing stable a 1G T-type calcium channel were plated on a 6 cm culture dish and grown for about 20 hours. Then, the medium was removed and the mixture of the supernatant of the transfected HEK293 cell culture with polybrene, as prepared above, was introduced. After about 6 hours of incubation, the medium was exchanged with fresh medium, and after about further 24 hours of incubation, the medium was again exchanged. After about 24 hours of incubation, 1 μg/ml of puromycin (Sigma) was added to the medium to selectively culture the cells having the puromycin resistance. After culturing the cells selectively during 14 days, the cell line expressing stable Kir2.1 could be obtained. Since the above used cells were selected with 1 mg/ml of G418, 1 mg/ml of G418 was added to the medium when culturing the cells.

EXAMPLE 3

Cell Membrane Voltage Determination

EPC-9 amplifier (HEKA, Germany) was used to determine a cell membrane voltage difference after expression of inwardly rectifying potassium (IRK)-type potassium channel, Kir2.1, in a single cell level by electrophysiological nystatin-perforated patch-clamp method. An extracellular solution for determining IRK-type potassium channel activity comprised KCl 10 mM, KOH 90 mM, L-aspartic acid 90 mM, $MgCl_2$ 1 mM, NaCl 1 mM and HEPES 10 mM (pH 7.4). An intracellular solution comprised NaCl 140 mM, KCl 3 mM, $MgCl_2$ 1 mM, $CaCl_2$ 1.5 mM, glucose 10 mM and HEPES 10 mM (pH 7.4).

For determining membrane voltage, the prepared intracellular solution was mixed with nystatin (250 μg/ml) and the resulting solution was introduced into a microglass electrode of 3–4 MΦ resistance. Then, the single cell was pricked with the electrode to determine the cell membrane voltage in a whole-cell recording mode.

FIG. 3 is a graph showing the membrane voltage of HEK293 cell wherein only $\alpha_{1G}$ T-type calcium channel is selectively expressed ($\alpha_{1G}$ HEK293 cell, control group), and HEK293 cell wherein $\alpha_{1G}$ T-type calcium channel and Kir 2.1 are co-expressed (Kir2.1+$\alpha_{1G}$ HEK293 cell). According to FIG. 3, the membrane voltage of $\alpha_{1G}$ HEK293 cell prior to the expression of Kir2.1 was about $-12.2 \pm 2.8$ mV (n=12). However, the membrane voltage of Kir2.1+$\alpha_{1G}$ HEK293 cell wherein Kir2.1 was expressed was about $-57.3 \pm 3.7$ mV (n=16). This indicated that the stable membrane voltage was formed by the Kir2.1 expression.

EXAMPLE 4

Determination of T-type Calcium Channel Activity and Kir2.1 Channel Activity EPC-9 amplifier (HEKA, Germany) was used to determine the current of T-type calcium channel in a single cell level by electrophysiological whole-cell patch-clamp method. An extracellular solution for determining T-type calcium channel activity comprised NaCl 140 mM, $CaCl_2$ 2 mM and HEPES 10 mM (pH 7.4), whereas an intracellular solution comprised KCl 130 mM, HEPES 10 mM, EGTA 11 mM and MgATP 5 mM (pH 7.4).

The prepared intracellular solution was introduced into a microglass electrode of about 3–4 MΦ resistance. Then, the single cell was pricked with the electrode to fix the cell membrane voltage as about −100 mV in a whole-cell recording mode. Thereafter, the inward current was determined, in which the current was induced by T-type calcium channel activity when the hypopolarization was caused by about −30 mV (50 ms duration) approximately every 10 seconds.

Further, the current of IRK-type potassium channel, Kir2.1 was also determined in a single cell level by the whole-cell patch-clamp method. An extracellular solution for determining IRK-type potassium channel activity comprised NaCl 135 mM, KCl 5.4 mM, $CaCl_2$ 1.8 mM, $MgCl_2$ 1 mM, HEPES 5 mM and glucose 10 mM (pH 7.4). An intracellular solution comprised D-gluconic acid (potassium salt form) 140 mM, $MgCl_2$ 2 mM, EGTA 1 mM, HEPES 5 mM and $Na_2ATP$ 1 mM (pH 7.4).

After the cell membrane voltage was fixed as about −60 mV in a whole-cell recording mode, −140 to −60 mV of 200 ms step pulse was applied to determine the inward current induced by potassium inwardly-rectifying channel activation of HEK293 cell.

FIG. 4 shows the results confiriming Kir2.1 expression in Kir2.1+$\alpha_{1G}$ HEK293 cell by using the electrophysiological whole-cell patch-clamp method. FIG. 4a ($\alpha_{1G}$ HEK293 cell) and FIG. 4b (Kir2.1+$\alpha_{1G}$ HEK293 cell) are graphs showing current-voltage correlation. FIG. 4c ($\alpha_{1G}$ HEK293 cell) and FIG. 4d (Kir2.1+$\alpha_{1G}$ HEK293 cell) show practical current curves at each voltage. When −140 to −60 mV of step pulse was applied, the potassium current was almost not indicated in $\alpha_{1G}$ HEK293 cell (FIG. 4c). Meanwhile, the potassium current was greatly indicated in Kir2.1+$\alpha_{1G}$ HEK293 cell due to the Kir2.1 expression (FIG. 4d). In case that the current activated at each voltage was re-plotted as current-voltage correlation graph, Kir2.1+$\alpha_{1G}$ HEK293 cell (FIG. 4b) showed again the inwardly-rectifying form, thus confirming the Kir2.1 expression.

Furthermore, the characteristics of Kir2.1 channel were analyzed by comparing with $IC_{50}$ value for $Ba^{2+}$ and $Cs^+$, the conventionally known IRK-type potassium channel inhibitor. For this, Kir2.1 channel activity determination method, as discussed above, was used and the inhibition by the known Kir2.1 inhibitor, $Ba^{2+}$ and $Cs^+$, was observed.

Figure 4E:
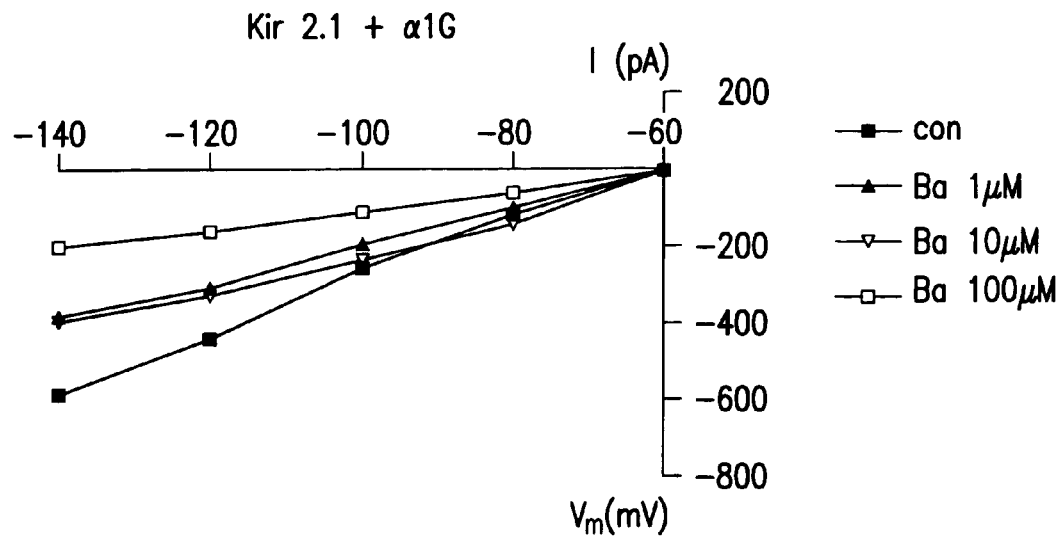
Figure 4F:
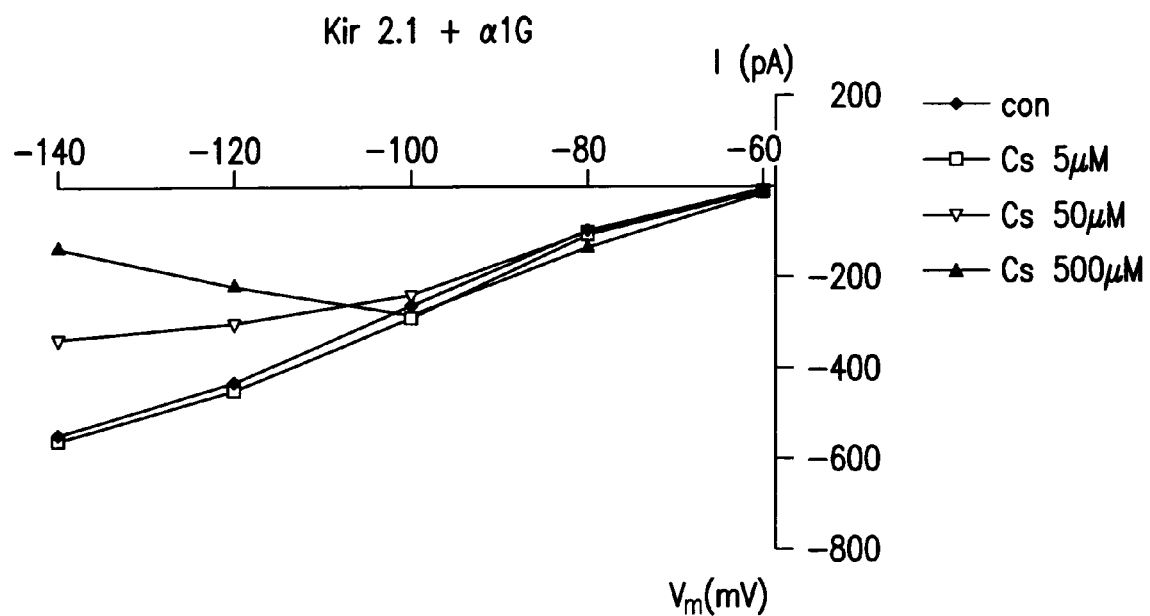

FIG. 4e and FIG. 4f are graphs showing the maximum current that occurred at each voltage when 1–100 μM $Ba^{2+}$ and 5–500 μM $Cs^+$ known as Kir2.1 inhibitor were administered to Kir2.1+$\alpha_{1G}$ HEK293 cell under −140 to −60 mV step pulse. It was re-confirmed that the Kir2.1 expression in Kir2.1+$\alpha_{1G}$ HEK293 cell was inhibited in a concentration-dependent manner by $Ba^{2+}$ and $Cs^+$ known as Kir2.1 inhibitor.

FIG. 5 shows that Kir2.1 expression does not change the pharmacological properties of $\alpha_{1G}$ T-type calcium channel. FIG. 5a ($\alpha_{1G}$ HEK293 cell) and FIG. 5b (Kir2.1+$\alpha_{1G}$ HEK293 cell) are graphs showing current-voltage correlation for $\alpha_{1G}$ T-type calcium channel activity. FIG. 5c ($\alpha_{1G}$ HEK293 cell) and FIG. 5d (Kir2.1+$\alpha_{1G}$ HEK293 cell) show practical current curves at each voltage, indicating that the current-voltage correlation for $\alpha_{1G}$ T-type calcium channel activity and the magnitude thereof were not changed by the Kir2.1 expression.

Furthermore, the characteristics of the channel were analyzed by comparing with $IC_{50}$ value for $Ni^{2+}$ and mibefradil, the conventionally known T-type calcium channel inhibitor. About 1 μM to 1 mM of $Ni^{2+}$ and about 0.1 to 10 μM of mibefradil were administered to the cell, respectively, according to the electrophysiological whole-cell patch-clamp method as described above, and then the inhibition (%) of the maximum of the inward current, caused through T-type calcium channel activated at or about −30 mV, was determined.

Figure 5A:
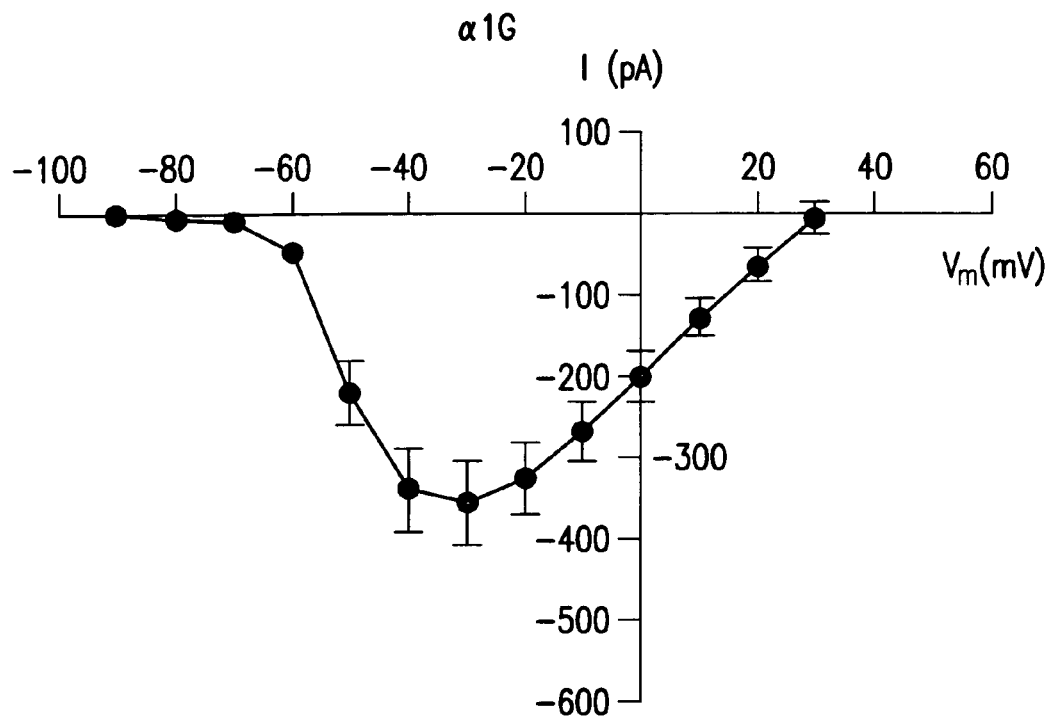
FIGS. 5a–5h show that Kir2.1 expression does not change the pharmacological properties of $\alpha_{1G}$ T-type calcium channel.
Figure 5B:
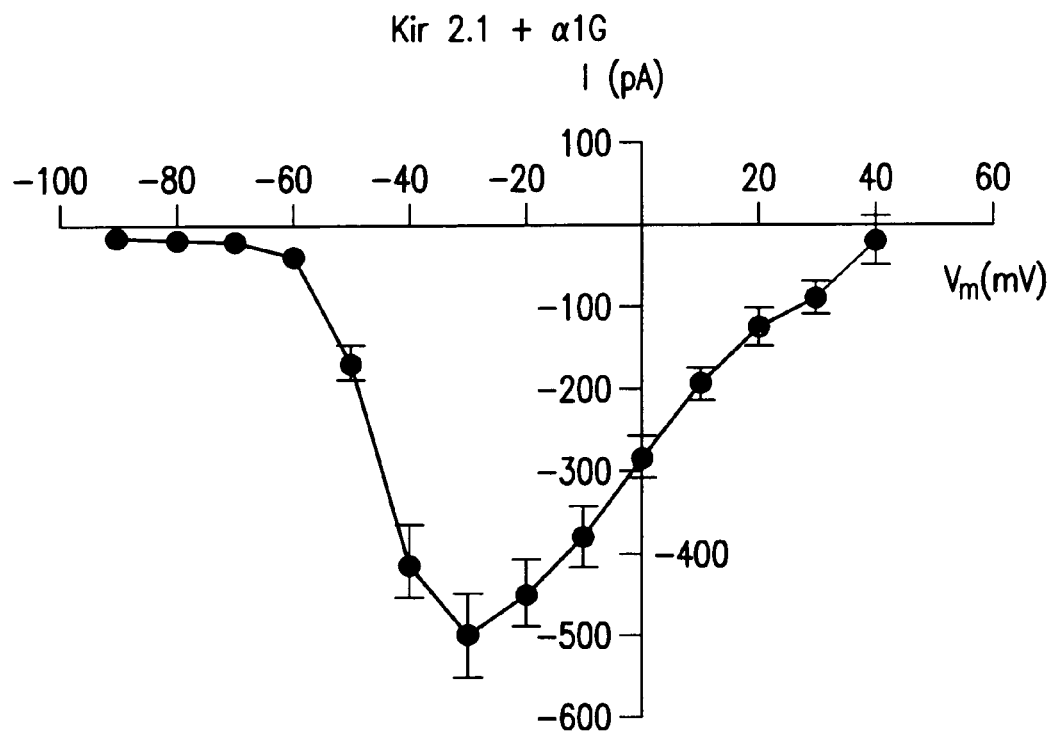
Figure 5C:
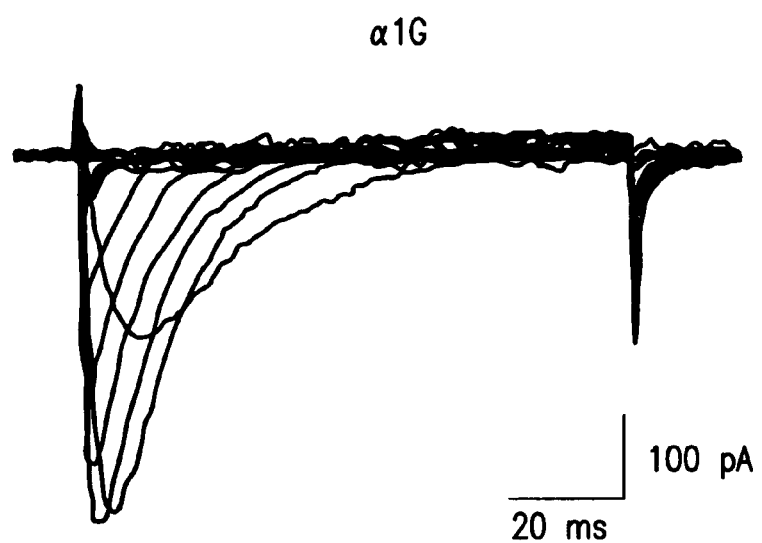
Figure 5D:
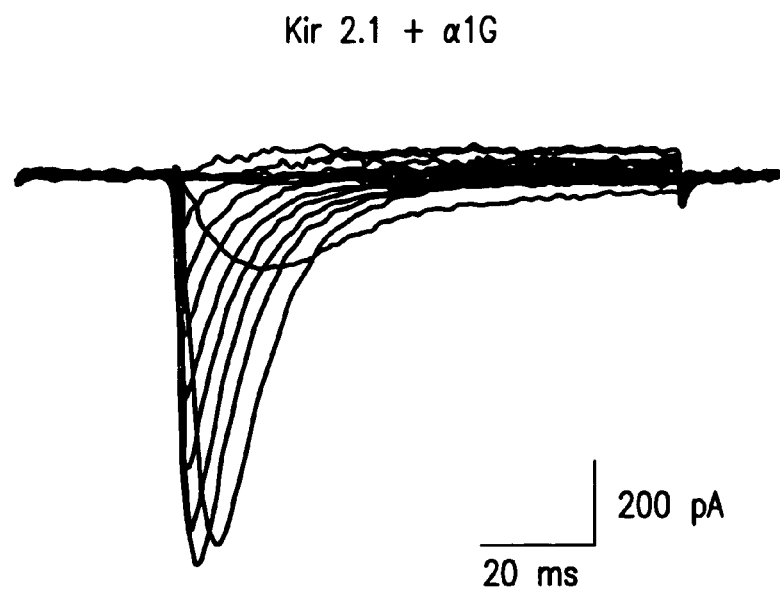
Figure 5E:
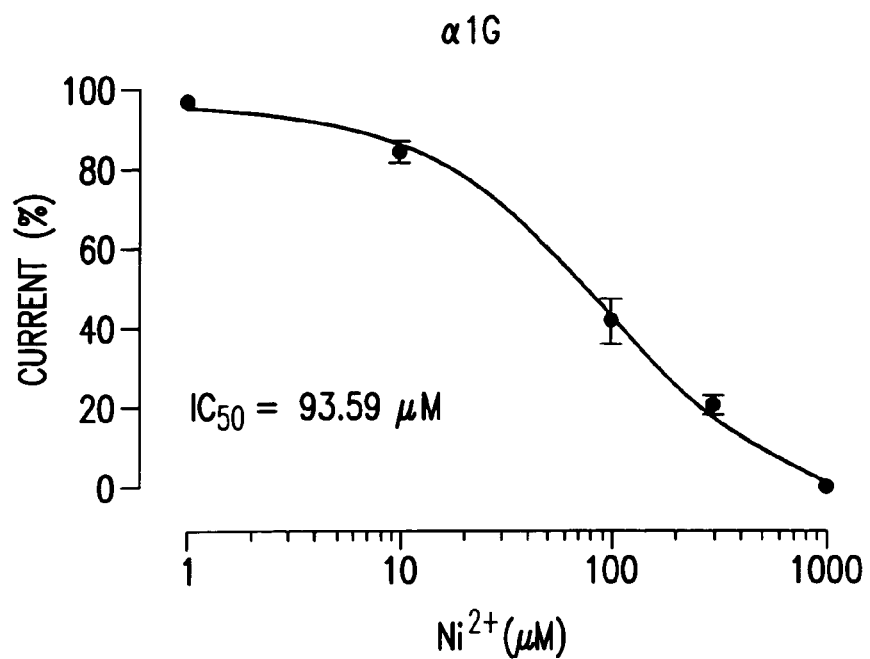
Figure 5F:
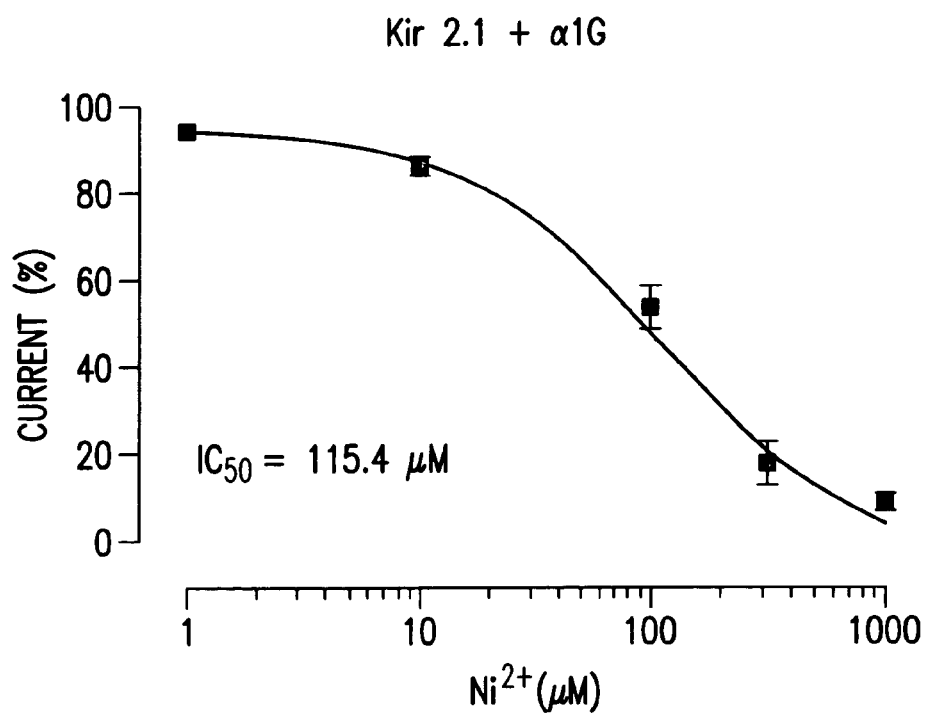
Figure 5G:
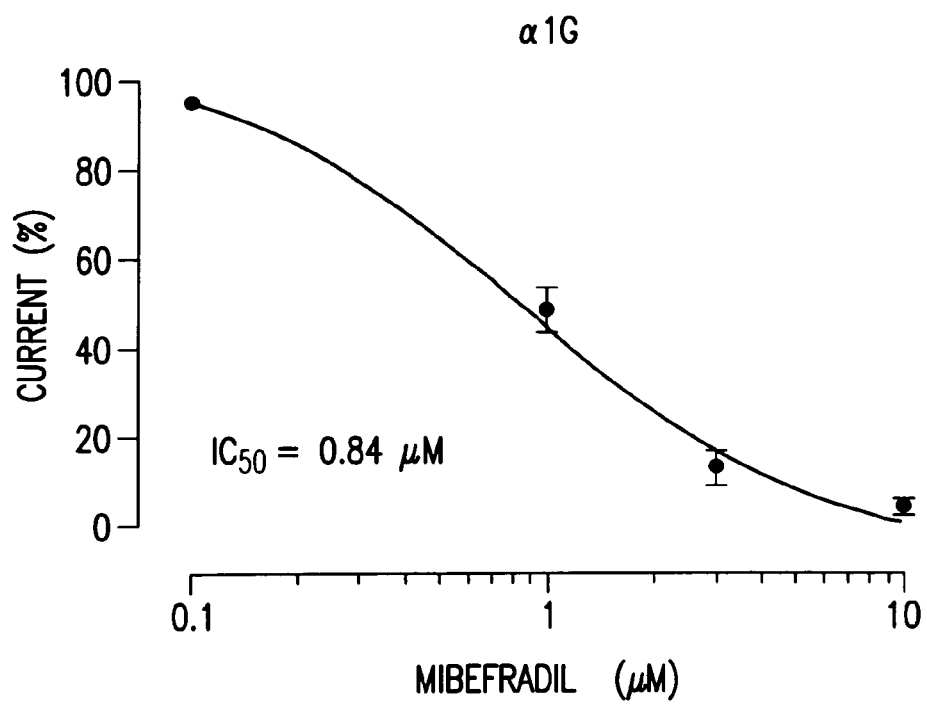
Figure 5H:
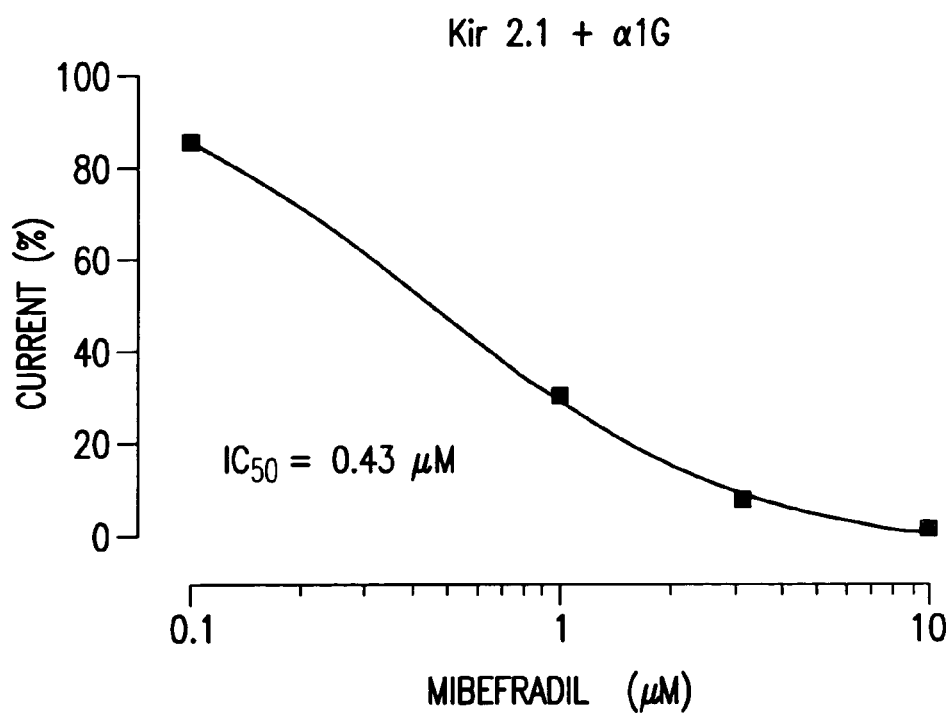

FIG. 5e ($\alpha_{1G}$ HEK293 cell) and FIG. 5f (Kir2.1+$\alpha_{1G}$ HEK293 cell) are graphs showing the inhibition (%) of the inward current depending on the concentration of $Ni^{2+}$ known as $\alpha_{1G}$ T-type calcium channel inhibitor. FIG. 5g ($\alpha_{1G}$ HEK293 cell) and FIG. 5h (Kir2.1+$\alpha_{1G}$ HEK293 cell) are graphs showing the current that is dependent on the mibefradil concentration. According to FIGS. 5e to 5h, Kir2.1+$\alpha_{1G}$ HEK293 cell is shown to have $IC_{50}$ values for $Ni^{2+}$ and mibefradil that are not significantly different from the values in $\alpha_{1G}$ HEK293 cell. This can be seen that the cell has the pharmacological properties of $\alpha_{1G}$ T-type calcium channel unchanged by Kir2.1 expression.

Figure 6A:
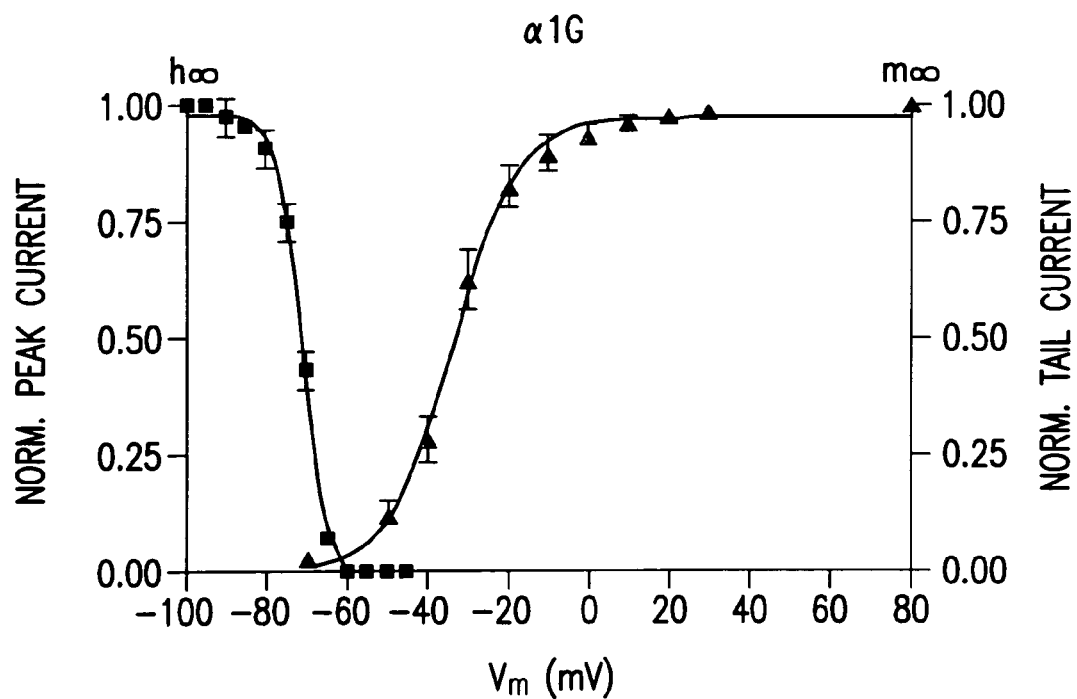
FIGS. 6a-6b show that the biophysiological properties of $\alpha_{1G}$ T-type calcium channel are not changed by Kir2.1 expression.
Figure 6B:
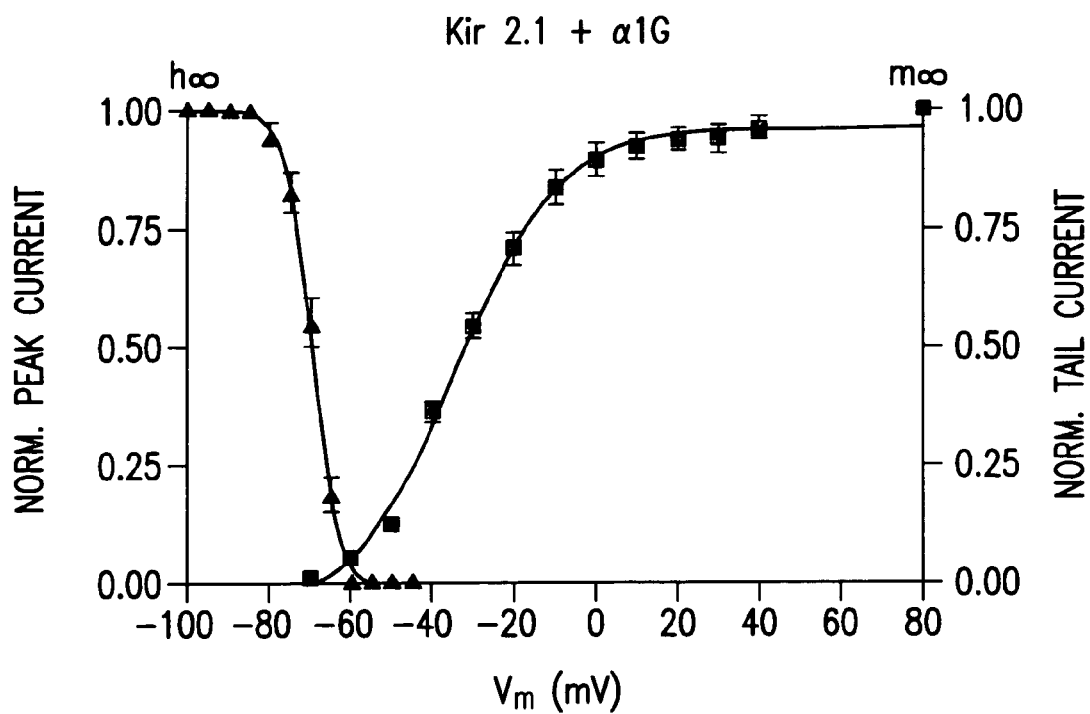

FIG. 6 shows that the biophysiological properties of $\alpha_{1G}$ T-type calcium channel are not changed by Kir2.1 expression. FIG. 6a ($\alpha_{1G}$ HEK293 cell) and FIG. 6b (Kir2.1+$\alpha_{1G}$ HEK293 cell) are graphs showing activation/inactivation of T-type calcium channel gate. The inactivation graph (h∞) was obtained by normalizing maximum inward current obtained under 100 ms step pulse at or about −30 mV after pre-depolarization condition of about −100 to −45 mV at 5 mV interval. The activation graph (m∞) was obtained by normalizing the tail-current obtained by applying −60 to +30 mV of step pulse after fixing the cell membrane valtage as −100 mV. From FIG. 6, it can be known that the characteristic activation and inactivation curve of T-type calcium channel are not changed substantially after the Kir2.1 expression.

Figure 7A:
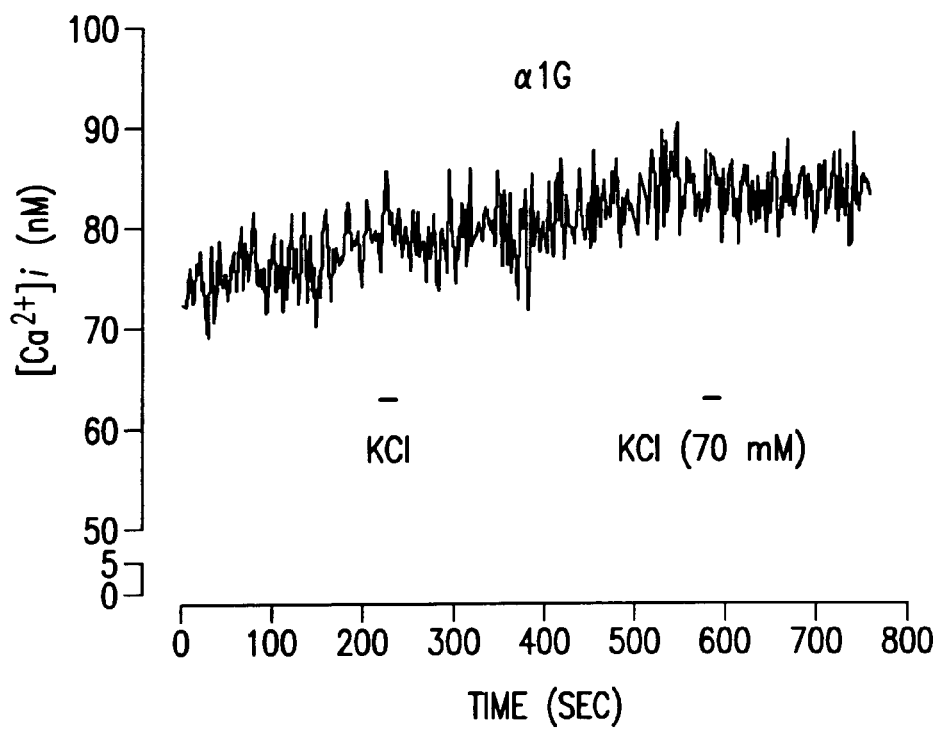
FIG. 7a is a graph showing that calcium influx is not changed by the treatment with 70 mM KCl in $\alpha_{1G}$ HEK293 cell.
Figure 7B:
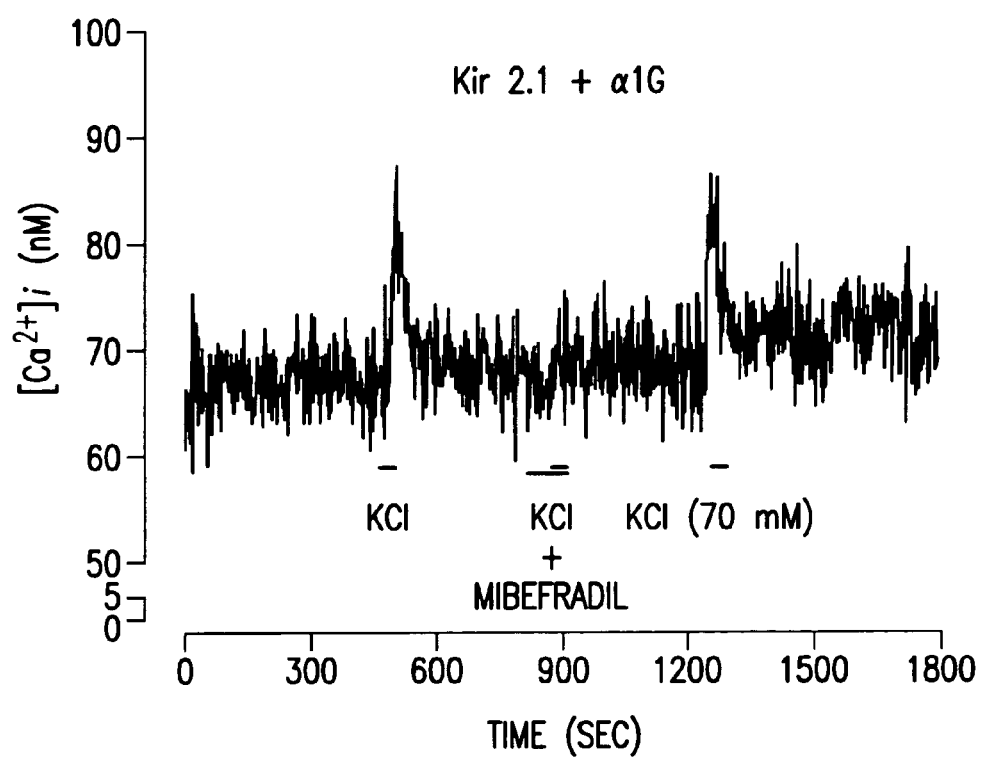
FIG. 7b is a graph showing that calcium influx is induced by T-type calcium channel activation which is caused by the treatment with 70 mM KCl in Kir2.1+$\alpha_{1G}$ HEK293 cell.

FIG. 7a is a graph showing that the treatment with 70 mM KCl does not change calcium influx in the control ($\alpha_{1G}$ HEK293 cell). FIG. 7b is a graph showing that calcium influx is induced by T-type calcium channel activated by treatment with 70 mM KCl in Kir2.1+$\alpha_{1G}$ HEK293 cell.

The calcium concentration in the cell was determined by using fura-2/AM as a fluorescent $Ca^{2+}$ label. The cells were primarily incubated with 5 μM fura-2/AM and 0.001% Pluronic F-127 in HEPES buffer solution (150 mM NaCl, 5 mM KCl, 1 mM $MgCl_2$, 2 mM $CaCl_2$, 10 mM HEPES, 10 mM glucose, pH 7.4) at a room temperature for about 40 to 60 minutes and then washed several times with HEPES buffer solution. After stablilzing the cells for about 10 minutes, the cells were selectively exposed to 340 nm and 380 nm by using an inverted microscope. Thereafter, the emitter fluorescence light that was entered through 515 nm long-pass filter was passed through a cooled CCD carmera. The light was converted into the intracellular calcium concentration by digital fluorescence analyzer to determine the calcium concentration.

Referring now to FIG. 7, it can be seen that the stable membrane voltage was formed by Kir2.1 expression in Kir2.1+$\alpha_{1G}$ HEK293 cell so that calcium influx could be induced by T-type calcium channel activated by treatment of a high concentration of KCl, and not by any electrophysiological method.

As seen above, since the cell line of the present invention responds sensitively to KCl and forms an appropriate level of the membrane voltage by which only T-type calcium channel is activated, the cell signaling pathway may be investigated by the molecular biological and biochemical studies. Furthermore, since mibefradil that was developed as T-type calcium channel inhibitor cannot be used clinically due to the side effects, the present invention is expected to facilitate T-type calcium channel inhibitor development by using the cell line in screening of lead compound for devoping a new drug, especially in high throughput screening (HTS) technologies.

What is claimed is:

1. A cell line which is deposited in the Korea Collection for Type Cultures under accession No. KCTC 10519BP.

* * * * *